United States Patent [19]

Hoss et al.

[11] Patent Number: 5,300,424
[45] Date of Patent: Apr. 5, 1994

[54] COMPOSITION FOR PRESERVATION OF DIAGNOSTIC TEST REAGENTS

[75] Inventors: Gerhard Hoss, Weilheim; Gunter Pappert, Tutzing; Axel Schmidt, München, all of Fed. Rep. of Germany

[73] Assignee: Boehringer Mannheim GmbH, Mannheim, Fed. Rep. of Germany

[21] Appl. No.: 729,332

[22] Filed: Jul. 12, 1991

[30] Foreign Application Priority Data

Jul. 18, 1990 [DE] Fed. Rep. of Germany ....... 4022878

[51] Int. Cl.$^5$ ............................................ G01N 33/53
[52] U.S. Cl. ..................................... 435/7.1; 252/380; 252/401; 252/405; 252/406; 435/810; 435/963; 435/967; 435/975; 436/8; 436/18; 436/176; 436/808; 436/826
[58] Field of Search ................ 435/7.1, 963, 967, 975, 435/810; 436/8, 18, 176, 826, 808; 426/262, 268, 269; 252/380, 397, 398, 399, 401, 405, 406

[56] References Cited

U.S. PATENT DOCUMENTS

| | | | |
|---|---|---|---|
| 4,040,977 | 8/1977 | Eggensperger et al. | 422/36 |
| 4,105,431 | 8/1978 | Lewis et al. | 548/213 |
| 4,868,139 | 9/1989 | Deeg et al. | 436/13 |
| 4,966,838 | 10/1990 | Ferrua et al. | 436/500 |

FOREIGN PATENT DOCUMENTS

| | | |
|---|---|---|
| 0029917 | 6/1981 | European Pat. Off. . |
| 0067394 | 12/1982 | European Pat. Off. . |
| 0375367 | 6/1990 | European Pat. Off. . |
| 2345164 | 10/1977 | France . |

OTHER PUBLICATIONS

Chemical Abstracts (1988) vol. 108, No. 21, p. 378.
Rosen, W. E., et al. (1984) Cosmet. Sci. Technol. pp. 191–205.
Ghannoum, M., et al. (1986) Folin Microbiol. 31:19–31.

Primary Examiner—David Saunders
Assistant Examiner—Christopher L. Chin

[57] ABSTRACT

The present invention is concerned with a combination for the preservation of diagnostic tests, characterized by a content of at least two components selected from the group comprising 2-methyl-4-isothiazolin-3-one hydrochloride, 2-hydroxypyridine-N-oxide, chloroacetamide, (N,N-methylene-bis-(N-(1-hydroxymethyl-2,5-dioxo-4-imidazolidinyl))-urea and 5-bromo-5-nitro-1,3-dioxan.

The present invention is also concerned with a preserved diagnostic test kit, comprising test reagents and at least two preservation agents selected from the group comprising 2-methyl-4-isothiazolin-3-one hydrochloride, 2-hydroxypyridine-N-oxide, chloroacetamide, (N,N-methylene-bis-(N-(1-hydroxymethyl)-2,5-dioxo-4-imidazolidinyl))-urea and 5-bromo-5-nitro-1,3-dioxan.

5 Claims, No Drawings

COMPOSITION FOR PRESERVATION OF DIAGNOSTIC TEST REAGENTS

The present invention is concerned with the preservation of diagnostic tests and especially of test kits by means of a combination of preservation agents, as well as with diagnostic tests which contain such agents.

Biological and especially diagnostic test kits usually contain, as reagents and as standards, substances which can be decomposed by micro-organisms. For the improvement of their storage stability, they must, therefore, be preserved by the manufacturer. However, hitherto it has proved to be extremely difficult to find appropriate preservatives for such diagnostics since, besides a sufficient effectiveness against bacteria, yeasts and fungi, the reactivity of the substances contained in the test must not be destroyed by the preservation agent. The sensitivity of proteins, for example enzymes or antibodies, as well as of antigens and substrates, towards preservation agents, is manifested, for example, in that the proteins can be denatured or the immunogenic structures are also destroyed. Furthermore, added preservation agents frequently bind such substances and thereby represent a competition for the actual binding component in the test (for example binding of enzyme/substrate, antibody/antigen). Therefore, hitherto it was necessary to find for a particular diagnostic test in each case a preservation agent which was precisely suitable therefor and which possesses the above-mentioned properties.

It is an object of the present invention to provide preservation agents which can be used quite generally in diagnostic tests, cover in their preserving properties a large spectrum of micro-organisms and minimise the formation of resistant micro-organisms. In this way, the testing and storage behaviour of preservation agents is to be limited to a few substances and the search for new preservation agents which display the above-described properties is to be reduced and dropped completely.

According to the present invention, this task is solved by a combination of preservation agents which are, in particular, suitable for the preservation of diagnostic tests and which have a content of at least two components selected from the group consisting of 2-methyl-4-isothiazolin-3-one hydrochloride, 2-hydroxypyridine-N-oxide, chloroacetamide, (N,N-methylene-bis-(N-(1-hydroxymethyl)-2,5-dioxo-4-imidazolidinyl))-urea and 5-bromo-5-nitro-1,3-dioxan.

Surprisingly, we have been able to show that the combination according to the present invention of at least two of the above-mentioned substances acts against a large spectrum of the most varied micro-organisms not only biocidally but thereby also, at the same time, shows no negative influence on the results of the diagnostic test process.

It is especially preferred to use 2-methyl-4-isothiazolin-3-one hydrochloride in combination with at least one of the above-mentioned preservation agents. Therefore, preservation agents are especially preferred which contain 2-methyl-4-isothiazolin-3-one hydrochloride and 2-hydroxypyridine-N-oxide or 2-methyl-4-isothiazolin-3-one hydrochloride and chloroacetamide or 2-methyl-4-isothiazolin-3-one hydrochloride and N,N-methylene-bis-(N-(1-hydroxymethyl)-2,5-dioxo-4-imidazolidinyl))-urea or 2-methyl-4-isothiazolin-3-one hydrochloride and 5-bromo-5-nitro-1,3-dioxan.

It is also preferred to combine 5-bromo-5-nitro-1,3-dioxan with, in each case, one of the other mentioned preservation agents.

2-Methyl-4-isothiazolin-3-one hydrochloride (hereinafter also designated methylisothiazoline) can be obtained by processes such as are described, for example, by S. N. Lewis et al., J. Heterocycl. Chem., 8, 571/1971 and in U.S. Pat. No. 4,105,431 (1968), hereby incorporated by reference. 2-Hydroxypyridine-N-oxide is marketed as a 20% solution under the name Oxy-pyrion by Pyrion-Chemie, Neuss, Federal Republic of Germany and can be isolated therefrom by extraction with ethyl acetate and/or chloroform and subsequent removal of the extraction agent by distillation. (N,N-Methylene-bis-(N-(1-hydroxymethyl)-2,5-dioxo-4-imidazolidinyl))-urea is marketed under the Trade Name Germall 115 by Chemag AG, Frankfurt, Federal Republic of Germany. 2-Chloroacetamide is obtainable from E. Merck, Darmstadt, Federal Republic of Germany. 5-Bromo-5-nitro-1,3-dioxan is marketed by Henkel KG, Federal Republic of Germany under the Trade Name Bronidox.

The anti-microbial effectiveness of these substances is known for individual and several micro-organisms. However, it is surprising that a combination thereof quite generally does not impair the highly sensitive reaction mechanisms such as take place in the case of biological and especially of diagnostic test processes.

Therefore, the present invention also provides diagnostic tests and especially diagnostic test kits which, as preservation agent, contain a combination of at least two substances selected from the group consisting of 2-methyl-4-isothiazolin-3-one hydrochloride, 2-hydroxypyridine-N-oxide, chloroacetamide and (N,N-methylene-bis-(N-(1-hydroxymethyl)-2,5-dioxo-4-imidazolidinyl))-urea and 5-bromo-5-nitro-1,3-dioxan.

The diagnostic test kits according to the present invention can contain the preservation agent in aqueous buffered solution or the preservation agent, together with the test reagents, can be in dry form.

In the tests preserved according to the present invention, 2-methyl-4-isothiazolin-3-one hydrochloride is preferably present in an amount of from 0.001 to 0.5%, 2-hydroxypyridine-N-oxide, chloroacetamide and (N,N-methylene-bis-(N-(1-hydroxymethyl)-2,5-dioxo-4-imidazolidinyl))-urea in an amount of from 0.1 to 0.5% and 5-bromo-5-nitro-1,3-dioxan in an amount of from 0.001 to 0.5%, referred to the concentration in the aqueous solution in which the test kit or the standard or buffer solutions are stored until used. We have found that the preservation agent combination according to the present invention in the test kit can be added not only to the buffer but also to the test reagent in question. However, it has also proved to be expedient simultaneously to add the preservation agent combination to the test reagents and to the buffer solutions. In the case of the test reagents in the test kit according to the present invention, these can be proteins, substrates, hormones, antigens and/or haptens and are usually biologically-active proteins and especially enzymes and/or antibodies and/or protein hormones, for example $T_3$ or $T_4$.

The present invention is also concerned with the use of the preservation agent combinations according to the present invention for the preservation of diagnostic tests.

The preservation agent combination according to the present invention has proved to be quite especially suitable for those tests which contain proteins, especially enzymes, antibodies and/or protein hormones, substrates for such enzymes, hormones, especially $T_3$, $T_4$ and steroids and/or antigens or haptens.

The following Examples are given for the purpose of illustrating the present invention:

EXAMPLE 1

1.1 Preparation of a mixed suspension of "bacteria"

*Escherichia coli* ATCC 8739, *Pseudomonas aeruginosa* ATCC 9027 and *Staphylococcus aureus* ATCC 6538 P are coated by means of an inoculation loop on to CaSo agar and cultured for 16 to 24 hours at 31° C. From the zone of the inoculation coating where confluent growth passes over into individual colonies, bacterial material originating from at least 5 colonies is removed by means of inoculation loops and suspended homogeneously in about 10 ml. of physiological saline. The suspension thus obtained is designated as test micro-organism suspension T.

The suspension T is so diluted with physiological saline that 10 ml. of inoculum suspension result with a colony count of $10^7$ KBE/ml. A spore suspension in distilled water of *Bacillus subtilis* is kept on hand, the titre of which is freshly determined every three months. For the preparation of the mixed suspension of "bacteria", the individual inoculum suspensions are mixed in equal parts. To this mixed suspension is added so much of spore suspension of *Bacillus subtilis* that $10^5$ spores per ml. result. This suspension is designated as mixed suspension of "bacteria".

2.2. Mixed suspension of "mould fungi and yeasts"

*Candida albicans* ATCC 10231, *Rhodotorula rubra* DSM 70403, *Aspergillus oryzae* DSM 6303, *Mucor racemosis* ATCC 7935 and *Penicillium frequentans* DSM 62843 are inoculated on to tilt agar test tubes containing Sabouraud maltose agar and cultured for 12 to 16 days at 23° C. The cultures are covered with about 2 ml. of physiological saline and slurried with the help of a sterile glass rod. The suspension which thus results is so diluted with sterile physiological saline that the turbidity corresponds to the McFarland standard $10^8$. This suspension is diluted 1:10 with sterile physiological saline from which results a suspension of about $10^7$ spores or yeast cells per ml. This suspension is designated as mixed suspension of "mould fungi and yeasts".

EXAMPLE 2

The components given in the following Table 1 of commercially available test kit solutions were investigated with the mixed suspensions prepared in Example 1.

Batch A 0.5 ml. of mixed suspension of "bacteria" are added per 50 ml. of the solution to be investigated. The batch thus contains about $10^5$ KBE/ml., the proportion of Bacillus subtilis thereby amounting to about $10^3$ KBE/ml. The storage temperature of the batch is 31° C.

Batch B 0.5 ml. of the mixed suspension of "mould fungi and yeasts" is added per 50 ml. of the solution to be investigated. The batch thus contains about $10^5$ KBE/ml. of mould fungi and yeasts. The storage temperature of the batch is 23° C.

After a storage period of 6 weeks, the colony count of batches A and B is determined. For this purpose, samples of 0.5 to 2 ml. are removed from the batches and, in two parallel dilution series, diluted with physiological saline corresponding to the expected micro-organism titre and the colony count is determined by plating out on nutrient agar plates. In each case, 0.1 ml. is distributed manually or by means of spiral plating apparatus on to standard agar plates (90 mm. diameter). The dilution depends upon the expected colony count.

The results obtained are given in the following Table 1. The values in this Table state by which number the micro-organisms are reduced by the addition of the preservation agent after a storage period of 6 weeks. The particular order numbers given in the Table indicate the order numbers of Boehringer Mannheim GmbH, Federal Republic of Germany.

The following abbreviations are used in the Tables:

| | |
|---|---|
| Brij 35 ® | tenside based on polyethylene glycol ethers of lauryl alcohol (manufacturer: Atlas Chemie) |
| POD | peroxidase |
| AFP | α-foetal protein |
| CEA | carcinoembryonic antigen |
| FSH | follicle-stimulating hormone |
| HCG | human chorionic gonadotropin |
| LM | luteinising hormone |
| MES | 4-morpholine-ethanesulphonic acid buffer |
| anti-progesterone-biotin | conjugate of biotin and an antibody against progesterone |
| PEG 40000/6000 | polyethylene glycol with an average molecular weight of 400000/6000 |
| anti-ApoAI | antibody against apolipoprotein AI |
| anti-ApoB | antibody against apolipoprotein B |

TABLE 1

| Test kit | Reagent composition (investigated components) | Micro-organism reduction KBE/ml. bacteria | mould fungi/yeasts |
|---|---|---|---|
| Cholinesterase Test-Combination order No. 127133 | bottle 1<br>phosphate buffer 52 mM; pH 7.7<br>5,5-dithiobisnitrobenzoate 0.25 mM<br>methylisothiazolone 0.01%<br>Germall 115 0.01% | $7 \times 10^4$ | $9.6 \times 10^4$ |
| Chloinesterase System package for Hitachi 704 order No. 851167 | bottle 1<br>phosphate buffer 60.7 mM; pH 7.7<br>5,5-dithiobisnitrobenzoate 0.30 mM<br>methylisothiazolone 0.001%<br>Germall 115 0.01% | $6.8 \times 10^4$ | $9.2 \times 10^4$ |
| Albumin automatic apparatus package order No. 263869 | succinate buffer 750 mM; pH 4.2<br>bromocresol green 1.5 mM<br>Brij 35<br>2-hydroxypyridine-N-oxide 1.0%<br>Germall 115 | $1.6 \times 10^4$ | $8.3 \times 10^4$ |

TABLE 1-continued

| Test kit | investigated components Reagent composition | Micro-organism reduction KBE/ml. bacteria | mould fungi/yeasts |
|---|---|---|---|
| Albumin System package for Hitachi 704 order No. 816272 | succinate buffer 75 mM; pH 4.2 bromocresol green 0.15 mM Brij 35 2-hydroxypyridine-N-oxide 0.1% Germall 115 0.01% | $3.6 \times 10^4$ | $7.0 \times 10^4$ |
| Saure Phosphatase Test Combination order No. 125008 | bottle 1 citrate buffer 550 mM; pH 4.8 methylisothiazolone 0.11% 2-hydroxypyridine-N-oxide 1.1% | $2 \times 10^4$ | $1.5 \times 10^5$ |
| Enzymun-Test AFP order No. 711411 | bottle 1 Incubation buffer phosphate buffer 40 mM; pH 6.6 methylisothiazolone 0.01% chloroacetamide 0.1% | $7.5 \times 10^4$ | $1.5 \times 10^4$ |
| | bottles 4a-e Standards AFP in human serum methylisothiazolone 0.1% 2-hydroxypyridine-N-oxide 0.1% | $1.1 \times 10^5$ | $6.2 \times 10^4$ |
| Enzymun-Test CEA order No. 204501 | bottle 1 Incubation buffer acetate buffer 100 mM; pH 5.7 methylisothiazolone 0.01% chloroacetamide 0.10% | $7.3 \times 10^4$ | $5.6 \times 10^4$ |
| | bottles 3a-e Standards CEA in horse serum methylisothiazolone 0.1% 2-hydroxypyridine-N-oxide 0.1% | $8.4 \times 10^5$ | $2.4 \times 10^4$ |
| Enzymun-Test Cortisol order No. 1096141 | bottle 1 Incubation buffer phosphate buffer 40 mM; pH 6.0 bovine serum albumin 0.30% methylisothiazolone 0.01% chloroacetamide 0.10% | $7.5 \: 10^4$ | $8.6 \times 10^4$ |
| | bottles 3a-e Standards Cortisol in human serum methylisothiazolone 0.1% 2-hydroxypyridine-N-oxide 0.1% | $1.1 \times 10^5$ | $6.2 \times 10^4$ |
| Enzymun-Test FSH order No. 1096923 | bottle 1 Incubation buffer phosphate buffer 40 mM; pH 7.4 methylisosthiazolone 0.01% 2-hydroxypyridine-N-oxide 0.1% | $7.5 \times 10^4$ | $8.6 \times 10^4$ |
| | bottles 3a-f Standards FSH in bovine serum matrix methylisothiazolone 0.01% 2-hydroxypyridine-N-oxide 0.1% | $9.4 \times 10^4$ | $7.2 \times 10^4$ |
| Enzymun-Test HCG order No. 855332 | bottle 1 Incubation buffer phosphate buffer 40 mM; pH 7.4 methylisothiazolone 0.01% chloroacetamide 0.10% | $7.5 \times 10^4$ | $8.6 \times 10^4$ |
| | bottles 4a-e Standards HCG in protein matrix methylisothiazolone 0.05% 2-hydroxypyridine-N-oxide 0.1% | $1.4 \times 10^5$ | $6.1 \times 10^4$ |
| Enzymun-Test IgE order No. 886882 | bottle 1 Incubation buffer Tris-buffer 100 mM; pH 7.6 methylisothiazolone 0.01% chloroacetamide 0.10% bottle 2 conjugate buffer Tris-buffer 100 mM; pH 7.6 | $9.6 \times 10^4$ | $7.6 \times 10^4$ |
| | bottles 4a-f Standards IgE in horse serum methylisothiazolone 0.1% 2-hydroxypyridine-N-oxide 0.1% | $8.4 \times 10^5$ | $2.4 \times 10^4$ |
| Enzymun-Test Insuline order No. 974 820 | bottle 1 Incubation buffer phosphate buffer 40 mM; pH 7.0 methylisothiazolone 0.01% chloroacetamide 0.1% | $7.5 \times 10^4$ | $8.6 \times 10^4$ |
| | bottles 3a-e Standards insulin in bovine serum matrix methylisothiazolone 0.1% 2-hydroxypyridine-N-oxide 0.1% | $9.4 \times 10^4$ | $7.2 \times 10^4$ |
| Enzymun-Test LH order No. 1096907 | bottle 1 Incubation buffer phosphate buffer 40 mM; pH 7.4 methylisothiazolone 0.01% chloroacetamide 0.1% | $7.5 \times 10^4$ | $8.6 \times 10^4$ |
| | bottles 3a-f Standards LH in bovine serum matrix methylisothiazolone 0.1% 2-hydroxypyridine-N-oxide 0.1% | $9.4 \times 10^4$ | $7.2 \times 10^4$ |
| Enzymun-Test Progesterone order No. 1204475 | bottle 1 conjugate buffer phosphate buffer 40 mM; pH 7.0 methylisothiazolone 0.01% | $7.5 \times 10^4$ | $8.6 \times 10^4$ |

TABLE 1-continued

| Test kit | investigated components Reagent composition | Micro-organism reduction KBE/ml. bacteria | mould fungi/yeasts |
|---|---|---|---|
| | chloroacetamide 0.1% bottle 2 POD conjugate POD ≧ 2 U/ml. MES 100 mM; pH 5.5 methylisothiazolone 0.01% chloroacetamide 0.1% | $6.5 \times 10^4$ | $8.1 \times 10^4$ |
| | bottle 3 AB-biotin anti-progesterone-biotin MES 100 mM; pH 5.5 methylisothiazolone 0.01% chloroacetamide | $6.5 \times 10^4$ | $8.1 \times 10^4$ |
| | bottles 4a-e Standards progesterone in human serum methylisothiazolone 0.1% 2-hydroxypyridine-N-oxide 0.1% | $1.1 \times 10$ | $6.2 \times 10^4$ |
| Enzymun-Test Testosterone order No. 1242024 | bottle 1 conjugate buffer phosphate buffer 40 mM; pH 7.0 methylisothiazolone 0.01% chloroacetamide 0.1% | $7.5 \times 10^4$ | $8.6 \times 10^4$ |
| | bottle 2 POD-conjugate POD ≧ 6.5 U/ml. MES 100 mM; pH 5.5 methylisothiazolone 0.01% chloroacetamide 0.1% | $6.5 \times 10^4$ | $8.1 \times 10^4$ |
| | bottle 3 AB-biotin anti-testosterone-biotin phosphate buffer 40 mM; pH 7.0 methylisothiazolone 0.01% chloroacetamide 0.1% | $7.5 \times 10^4$ | $8.6 \times 10^4$ |
| | bottles 4a-e Standards testosterone in bovine serum matrix methylisothiazolone 0.1% 2-hydroxypyridine-N-oxide 0.1% | $9.4 \times 10^4$ | $7.2 \times 10^4$ |
| Tinaquant a Apolipoprotein AI order No. 1174371 | bottle 1 Tris buffer 50 mM; pH 8.0 PEG 40000 4.00% methylisosthiazolone 0.1% Bronidox 0.10% | $5.3 \times 10^4$ | $6.6 \times 10^4$ |
| | bottle 2 Tris buffer 100 mM; pH 8.0 anti-ApoAI (sheep) methylisothiazolone 0.1% Bronidox 0.10% | $5.3 \times 10^4$ | $6.6 \times 10^4$ |
| | calibrator human serum methylisothiazolone 0.01% Bronidox 0.10% | $5.5 \times 10^4$ | $5.4 \times 10^4$ |
| Tinaquant a Apolipoprotein B order No. 1174380 | bottle 1 Tris buffer 50 mM; pH 8.0 PEG 6000 4.00% methylisothiazolone 0.01% Bronidox 0.10% | $5.3 \times 10^4$ | $6.6 \times 10^4$ |
| | bottle 2 Tris buffer 100 mM; pH 8.0 Anti-ApoB (sheep) methylisothiazolone 0.1% Bronidox 0.10% | $5.3 \times 10^4$ | $6.6 \times 10^4$ |
| | calibrator human serum methylisothiazolone 0.1% Bronidox 0.10% | $5.5 \times 10^4$ | $5.4 \times 10^4$ |
| Reagent for the determination of albumin in urine (Tinaquanta order No. 1203622) | bottle 1 Tris buffer 100 mM; pH 8.0 PEG 40000 4.00% methylisothiazolone 0.1% Bronidox 0.10% | $3.1 \times 10^4$ | $5.5 \times 10^4$ |
| | bottle 2 Tris buffer 100 mM; pH 7.2 Anti-hSA (sheep) methylisothiazolone 0.01% Bronidox 0.10% | $3.1 \times 10^5$ | $5.5 \times 10^4$ |
| | calibrator phosphate buffer 50 mM; pH 8.0 serum albumin 300 mg/l methylisothiazolone 0.01% Bronidox 0.10% | $3.1 \times 10^5$ | $5.5 \times 10^4$ |

5. Micro-organism reduction

5.1. Bacteria

The colony count is to decrease in the course of the period of observation by at least $10^3$ KBE and no significant increase of micro-organisms must occur.

5.2. Mould fungi/yeasts

The colony count is to decrease in the course of the period of observation by at least $10^2$ KBE and no significant increase of micro-organisms must occur.

6. Assessment

The preservation is sufficient when the requirements according to point 5 are fulfilled. In this case, it is to be expected that the protective action of the preservation is sufficient against contamination which occurs in the case of filling under non-sterile conditions or in the case of the usual handling of these reagents (atmospheric microbes, microbes on the hands, non-sterile pipettes and non-sterile packing agents).

7. Influence on the diagnostic test process

None of the combinations used of preservation agents show any influence on the measurement results of the diagnostic tests according to Table 1.

It will be understood that the specification and examples are illustrative but not limitative of the present invention and that other embodiments within the spirit and scope of the invention will suggest themselves to those skilled in the art.

We claim:

1. In a diagnostic test kit containing diagnostic test reagents for determination of an analyte the improvement comprising a preservation reagent in said diagnostic test reagents or in a buffer solution, wherein said preservation reagent consists of 2-hydroxypyridine-N-oxide in an active concentration of from 0.1 to 0.5% and at least one other reagent selected from the group consisting of 2-methyl-4-isothiazoline-3-one hydrochloride, chloroacetamide, (N,N-methylene-bis-(N-1-hydroxymethyl)-2,5-dioxo-4-imidazolidinyl))-urea and 5-bromo-5-nitro-1,3-dioxane.

2. In a diagnostic test kit containing diagnostic test reagents for determination of an analyte the improvement comprising a preservation reagent in said diagnostic test reagents or in a buffer solution, wherein said preservation reagent consists of chloroacetamide in an active concentration of from 0.1 to 0.5% and at least one other reagent selected from the group consisting of 2-methyl-4-isothiazoline-3-one hydrochloride, 2-hydroxypyridine-N-oxide, (N,N-methylene-bis-(N-1-hydroxymethyl)-2,5-dioxo-4-imidazolidinyl))-urea and 5-bromo-5-nitro-1,3-dioxane.

3. In a diagnostic kit containing diagnostic test reagents for determination of an analyte the improvement comprising a preservation reagent in said diagnostic test reagents or in a buffer solution, wherein said preservation reagent consists of 2-methyl-4-isothiazoline-3-one hydrochloride and chloroacetamide.

4. In a diagnostic kit containing diagnostic test reagents for determination of an analyte the improvement comprising a preservation reagent in said diagnostic test reagents or in a buffer solution, wherein said preservation reagent consists of 2-methyl-4-isothiazoline-3-one hydrochloride and 2-hydroxypyridine-N-oxide.

5. In a diagnostic kit containing diagnostic test reagents for determination of an analyte the improvement comprising a preservation reagent in said diagnostic test reagents or in a buffer solution, wherein said preservation reagent consists of 2-hydroxypyridine-N-oxide and (N,N-methylene-bis-(N-1-hydroxymethyl)-2,5-dioxo-4-imidazolidinyl))-urea.

* * * * *